US005858673A

United States Patent [19]
Price et al.

[11] Patent Number: 5,858,673
[45] Date of Patent: Jan. 12, 1999

[54] METHOD FOR DETECTING PROSTATE CELLS

[75] Inventors: Douglas K. Price, Mooresville; Chris M. Teigland, Charlotte, both of N.C.

[73] Assignee: Charlotte-Mecklenburg Hospital Authority, Charlotte, N.C.

[21] Appl. No.: 851,135

[22] Filed: May 5, 1997

Related U.S. Application Data

[60] Provisional application No. 60/016,543 Jun. 24, 1996.

[51] Int. Cl.$^6$ ....................................................... C12Q 1/68
[52] U.S. Cl. ............................ 435/6; 435/91.1; 435/91.2; 536/24.3; 536/24.33
[58] Field of Search .............................. 435/6, 91.1, 91.2, 435/695; 536/24.3, 24.31, 24.32, 24.33

[56] References Cited

U.S. PATENT DOCUMENTS

| | | | |
|---|---|---|---|
| 5,198,338 | 3/1993 | Croce | 435/6 |
| 5,227,471 | 7/1993 | Wright, Jr. | 530/388.8 |
| 5,242,795 | 9/1993 | Croco | 435/6 |
| 5,314,996 | 5/1994 | Wright, Jr. | 530/387.3 |
| 5,330,892 | 7/1994 | Vogelstein et al. | 435/6 |
| 5,362,623 | 11/1994 | Vogelstein et al. | 435/6 |
| 5,380,645 | 1/1995 | Vogelstein | 435/6 |
| 5,382,510 | 1/1995 | Levine et al. | 435/6 |
| 5,387,676 | 2/1995 | Zavada et al. | 536/23.5 |
| 5,411,860 | 5/1995 | Vogelstein et al. | 435/6 |
| 5,449,605 | 9/1995 | Smulson et al. | 435/6 |
| 5,550,040 | 8/1996 | Purohit et al. | 435/91.2 |
| 5,702,901 | 12/1997 | Cummins et al. | 435/6 |

FOREIGN PATENT DOCUMENTS

95/28498  10/1995  WIPO.

OTHER PUBLICATIONS

Reubel et al. Arch. Virol. vol. 140, pp. 1049–1060, 1995.
Cassinotti et al. J. Med. Virol. vol. 50, pp. 75–81, 1996.
Israeli et al. The Journal of Urology. vol. 153, pp. 573–577, Mar. 1995.
Israeli et al. Cancer Research. vol. 53, pp. 337–230, Jan. 1993.
A. Lundwall, Molecular cloning of human prostate specific antigen cDNA, Apr. '87, pp. 317–323.
Jose G. Moreno et. al., Detection of Hematogenous Micrometastasis in Patients with Prostate Cancer, Nov. 1, 1992, pp. 6110–6112.
Aaron E. Katz, M.D. et al., Molecular Staging of Prostate Cancer with the Use of an Enhanced Reverse Transcriptase–PCR Assay, Jun. 1994, pp. 765–775.
Michael V. Seiden et al., Detection of Circulating Tumor Cells in Men With Localized Prostate Cancer, Dec. 1994, pp. 2634–2639.
Ron S. Israeli et al., Sensitive Nested Reverse Transcription Polymerase Chain Reaction Detection of Circulating Prostatic Tumor Cells: Comparison of Prostate–specific Membrane Antigen and Prostate–specific Antigen–based Assays, Dec. 15, 1994, pp. 6306–6310.
Aaron E. Katz et al., Enhanced Reversed Transcriptase–Polymerase Chain Reaction for Prostate Specific Antigen as an Indicator of True Pathologic Stage in Patients with Prostate Cancer, Apr. 1, 1995, pp. 1642–1648.
Cristoforo Cama et al., Molecular Staging of Prostate Cancer. II. A Comparison of the Application of an Enhanced Reverse Transcriptase Polymerase Chain Reaction Assay for Prostate Specific Antigen Versus Prostate Specific Membrane Antigen, May 1995, pp. 1373–1378.
Ronald A. Ghossein et al., Detection of Circulating Tumor Cells in Patients With Localized and Metastatic Prostatic Carcinoma: Clinical Implications, May 1995, pp. 1195–1200.
Sylvain Loric et al., Enhanced Detection of Hematogenous Circulating Prostatic Cells in Patients with Prostate Adenocarcinoma by Using Nested Reverse Transcription Polymerase Chain Reaction Assay Based on Prostate–Specific Membrane Antigen, 1995, pp. 1698–1704.

*Primary Examiner*—James Ketter
*Assistant Examiner*—Irem Yucel
*Attorney, Agent, or Firm*—Bell Seltzer Intellectual Property Law Group of Alston & Bird LLP

[57] ABSTRACT

There is provided a sensitive multiplex RT-PCR assay for the detection of circulating prostate antigen expressing cells. Multiplex PCR uses multiple sets of primers to concurrently amplify different DNA sequences that can be readily resolved by gel electrophoresis. When applied to blood samples from prostate cancer patients, the nested multiplex RT-PCR can simultaneously detect PSA-expressing cells, PSM-expressing cells, and a ubiquitously expressed internal PCR control gene, glyceraldehyde 3-phosphate dehydrogenase (G3PDH), all within a single reaction.

13 Claims, 7 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic oligonucleotide
        ( P r i m e r    P S A 5 ' )"

( x i ) SEQUENCE DESCRIPTION: SEQ ID NO:1:

GATGACTCAG CCACGACCT                                                                          1 9

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic oligonucleotide
            ( p r i m e r    P S A 3 ' )"

( x i ) SEQUENCE DESCRIPTION: SEQ ID NO:2:

CACAGACACC CCATCCTATC                                                                2 0

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic oligonucleotide
        ( P r i m e r    P S A F 1 )"

( x i ) SEQUENCE DESCRIPTION: SEQ ID NO:3:

CTGTCAGAGC CTGCCGAGCT C                                                                 21

( 2 ) INFORMATION FOR SEQ ID NO:4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic oligonucleotide
    ( P r i m e r   P S A R 1 )"

( x i ) SEQUENCE DESCRIPTION: SEQ ID NO:4:

GATATGTCTC CAGGCATGGC C                                                                 21

( 2 ) INFORMATION FOR SEQ ID NO:5:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic Oligonucleotide
    ( P r i m e r   P S M 5 ' )"

( x i ) SEQUENCE DESCRIPTION: SEQ ID NO:5:

CAATGAAGCT ACTAACATTA CTCC                                                              24

( 2 ) INFORMATION FOR SEQ ID NO:6:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic oligonucleotide
    ( P r i m e r   P S M 3 ' )"

( x i ) SEQUENCE DESCRIPTION: SEQ ID NO:6:

TCGGAGTAGA GAATGACTCC TTTG                                                              24

( 2 ) INFORMATION FOR SEQ ID NO:7:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic oligonucleotide
     ( p r i m e r   P S M F 1 )"

( x i ) SEQUENCE DESCRIPTION: SEQ ID NO:7:

CAGATACCAC ATTTAGCAGG AAC                                                               23

( 2 ) INFORMATION FOR SEQ ID NO:8:

( i ) SEQUENCE CHARACTERISTICS:
    ( A ) LENGTH: 22 base pairs
    ( B ) TYPE: nucleic acid
    ( C ) STRANDEDNESS: single (D) TOPOLOGY: linear (ii) MOLECULE TYPE: other nucleic acid
    (A) DESCRIPTION: /desc = "Synthetic oligonucleotide (Primer PSMR1)"

(xi) SEQUENCE DESCRIPTION: SEQ ID NO:8:

CATATCCTGG AGGAGGTGGT TC    22

(2) INFORMATION FOR SEQ ID NO:9:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic oligonucleotide (Primer G3PDH5')"

(xi) SEQUENCE DESCRIPTION: SEQ ID NO:9:

TGAAGGTCGG AGTCAACGGA TTTGGT    26

(2) INFORMATION FOR SEQ ID NO:10:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic oligonucleotide (Primer G3PDH3')"

(xi) SEQUENCE DESCRIPTION: SEQ ID NO:10:

CATGTGGGCC ATGAGGTCCA CCAC    24

(2) INFORMATION FOR SEQ ID NO:11:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic oligonucleotide (Primer PSAF2)"

(xi) SEQUENCE DESCRIPTION: SEQ ID NO:11:

CATGCTGTGT GCTGGACGCT GGAC    24

(2) INFORMATION FOR SEQ ID NO:12:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic oligonucleotide (Primer PSMF2)"

(xi) SEQUENCE DESCRIPTION: SEQ ID NO:12:

CTGGATTCTG TTGAGCTAGC AC    22

METHOD FOR DETECTING PROSTATE CELLS

CROSS REFERENCE TO RELATED APPLICATION

This application claims the benefit of U.S. Provisional Patent Application Serial No. 60/016,543, filed Jun. 24, 1996 (by Petition To Correct Filing Date filed under separate cover concurrently herewith).

BACKGROUND OF THE INVENTION (1) Field of the Invention

The present invention relates to a method for detecting prostate cells. More specifically, this invention relates to a method for detecting circulating prostate cells using a nested multiplex reverse transcriptase polymerase chain reaction assay.

(2) The Prior Art

Adenocarcinoma of the prostate is the most common internal cancer in males with an estimated 244,000 new cases per year and 38,000 deaths. (P. A. Wingo, et al., *Ca. Cancer J. Clin.* 45: 8–30 (1995)). The diagnostic tools of serum prostate-specific antigen (PSA) level, digital rectal exam, transrectal prostatic ultrasound, sextant needle biopsies, histologic Gleason scoring, computed tomography, and magnetic resonance imaging currently provide the foundation for the clinical staging of prostate cancer.

If the disease is truly confined to the prostate, surgical removal of the gland should remove all traces of malignant cells. However, it has been shown that up to 40% of patients diagnosed preoperatively with prostate-confined disease using current modalities actually have disease outside the margins of surgical resection at surgery. (Lu-Yao, McIerran, Wasson, Wennberg. An assessment of radical prostatectomy. Time trends, geographic variation and outcomes. The Prostate Patent Outcome Research Team, *JAMA* 269:2633–2655 (1993); Voges, et al., Morphologic analysis of surgical margins with positive findings in prostatectomy for adenocarcinoma of the prostate, *Cancer* 69:520–526 (1992); Catalona et al., Nerve-sparing radical prostatectomy: extraprostatic tumor extension and preservation of erectile function, *J. Urol.* 134:1149–1151 (1985); Epstein, et al., Is tumor volume an independent predictor of progression following radical prostatectomy? A multivariate analysis of 185 clinical stage B adenocarcinoma of the prostate with 5 years of follow-up, *J. Urol.* 148:1478–1481 (1993)). This understaging of males exposes them to the morbidity of radical surgery without providing a cure.

An RT-PCR assay for PSA has been developed by Katz and co-workers which recognizes PSA-expressing cells. The RT-PCR assay uses PSA primers to detect prostate cells in the peripheral circulation prior to radical prostatectomy. (A. E. Katz, et al, Molecular Staging of prostate Cancer With the Use of an enhanced Reverse Transcriptase-PCR Assay, *Urology* 43:765–775 (1994)). This PSA assay detects only PSA antigens.

Another assay for detecting occult hematogenous micrometastatic prostatic cells is a modification of similar PCR assays uses PCR primers derived from the cDNA sequences of prostate-specific membrane (PSM) antigen. (R. S. Israeli, et al, Sensitive Nested Reverse Transcription Polymerase Chain Reaction Detection Of Circulating Prostatic Tumor Cells: Comparison Of Prostate-Specific Membrane Antigen And Prostate-Specific Antigen-Based Assays, *Cancer Research* 53:227–230 (1993)). This PSM assay detects only PSM antigens.

Even in view of these advances in prostate cancer cell detection, there still remains a need for better identification of prostate tumor antigens. In particular there is need for a single assay to detect the presence of both PSM and PSA antigens.

SUMMARY OF THE INVENTION

An object of the present invention is to provide a method for the detection of one prostatic cell within a population of 1,000,000 lymphocytes.

Another object of this invention is to provide a single assay for detecting the mRNA expression of both PSA and PSM genes.

In accordance with the present invention there is described a method for detecting circulating prostate cells in a human. In one embodiment, the invention is directed to obtaining a blood sample of a human, isolating total cellular RNA from the blood synthesizing a first strand cDNA by reverse transcription, adding a portion of the first strand cDNA product to a master mix containing PSM and PSA outside primers, adding polymerase to the master mix and amplifying, adding a portion of the first strand cDNA product to the master mix containing PSM and PSA inside primers, adding Taq polymerase to the master mix and amplifying the product, then nesting the amplified portion with a second set of primers, and comparing the blood sample to a positive control.

The present invention also encompasses kits for in vitro or in vivo applications for diagnosis of prostate carcinoma.

DETAILED DESCRIPTION OF THE INVENTION

The present invention is directed to an assay for diagnosing circulating prostate cells.

A nested multiplex reverse transcriptase PCR assay was developed to simultaneously detect PSA-expressing prostatic cells, PSM-expressing prostatic cells and an internal control (G3PDH). The primers used for this assay are listed in Table 1.

Primers used in the PSM reactions were chosen for their ability to optimally amplify PSM without interference from the PSA and G3PDH primers contained within the multiplex reaction, and to amplify a fragment that could be easily resolved from either PSA or G3PDH by electrophoresis. Primers used for the initial outside PSM reaction (PSM5' nucleotides 398–422 (SEQ ID No. 5) and PSM3' nucleotides 927–950 (SEQ ID No. 6)) were intentionally chosen upstream of the reported homology with the human transferrin receptor to avoid any possible false amplification. R. S. Israeli, et al, Molecular Cloning of a Complementary DNA encoding a Prostate-Specific Membrane Antigen, *Cancer Research* 54:6306–6310 (1994). Nested PSM primers (PSMF1 nucleotides (SEQ ID No. 7) 496–518 and PSMR1 nucleotides 694–715 (SEQ ID No. 8)), were located internal to the initial primers 73 bps and 210 bps, respectively. Due to the currently unknown intron/exon structure of the PSM gene, these primer sets are not known to span in intron. However, PCR of human genomic DNA with either PSM primer set was unsuccessful in amplifying the products predicted from the cDNA sequence, thus it is assumed that at least one intron is spanned by these primers. The PCR primers used for the amplification of the internal control, G3PDH, were purchased commercially and are known to span several introns.

Experimental

Patient selection

Patients were recruited from the McKay Department of Urology of the Carolinas Medical Center. Metastatic prostate cancer patients were defined by a serum PSA test level greater than 20, no prior or current hormonal treatment, and bone metastasis as indicated by a positive bone scan. Hormone-refractory prostate cancer patients were defined

TABLE 1

Sequences of primers used for
Nested Multiplex PCR and Southern blots

| Name | 5'-3' Sequence | PCR product |
|---|---|---|
| PSA5' (SEQ ID NO.1) | GATGACTCAGCCACGACCT | 710 bp |
| PSA3' (SEQ ID NO.2) | CACAGACACCCCATCCTATC | |
| PSAF1 (SEQ ID NO.3) | CTGTCAGAGCCTGCCGAGCTC | 634 bp |
| PSAR1 (SEQ ID NO.4) | GATATGTCTCCAGGCATGGCC | |
| PSM5' (SEQ ID NO.5) | CAATGAAGCTACTAACATTACTCC | 552 bp |
| PSM3' (SEQ ID NO.6) | TCGGAGTAGAGAATGACTCCTTTG | |
| PSMF1 (SEQ ID NO.7) | CAGATACCACATTTAGCAGGAAC | 219 bp |
| PSMR1 (SEQ ID NO.8) | CATATCCTGGAGGAGGTGGTTC | |
| G3PDH5' (SEQ ID NO.9) | TGAAGGTCGGAGTCAACGGATTTGGT | 983 bp |
| G3PDH3 (SEQ ID NO.10) | CATGTGGGCCATGAGGTCCACCAC | |
| PSAF2 (SEQ ID NO.11) | CATGCTGTGTGCTGGACGCTGGAC | |
| PSMF2 (SEQ ID NO.12) | CTGGATTCTGTTGAGCTAGCAC | |

Figure 1:
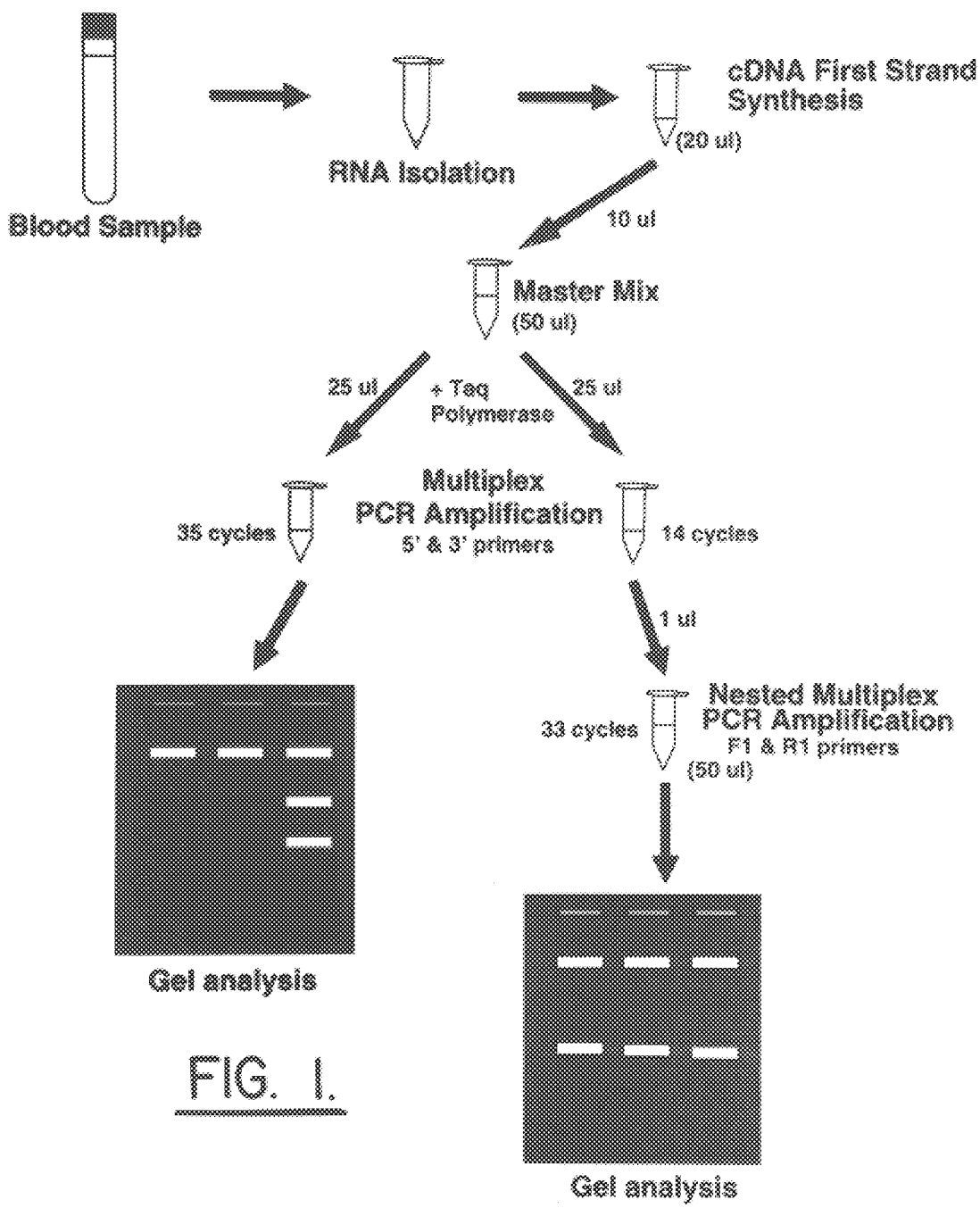
FIG. 1 is a flow chart of the nested multiplex RT-PCR assay to detect circulating prostate cancer cells.
Figure 2A:
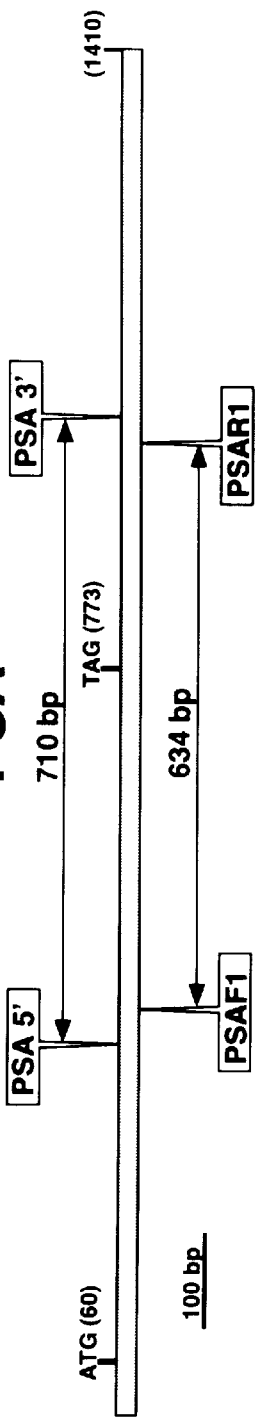
FIG. 2A is a cDNA map for prostate specific antigen.
Figure 2B:
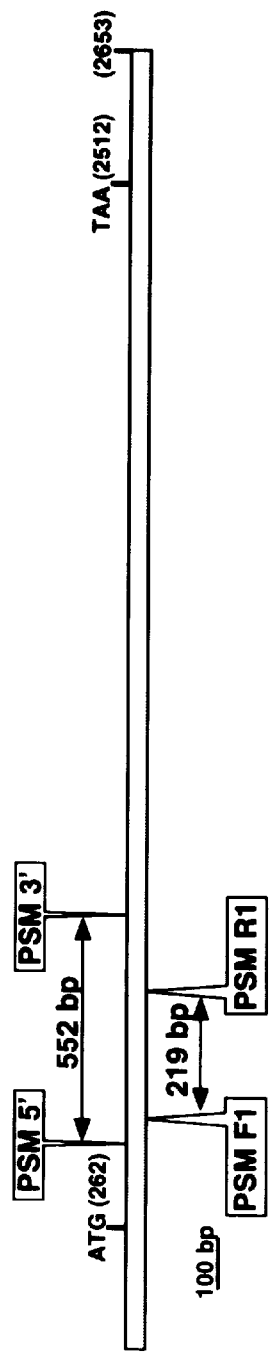
FIG. 2B is a cDNA map for prostate specific membrane antigen.
Figure 2C:
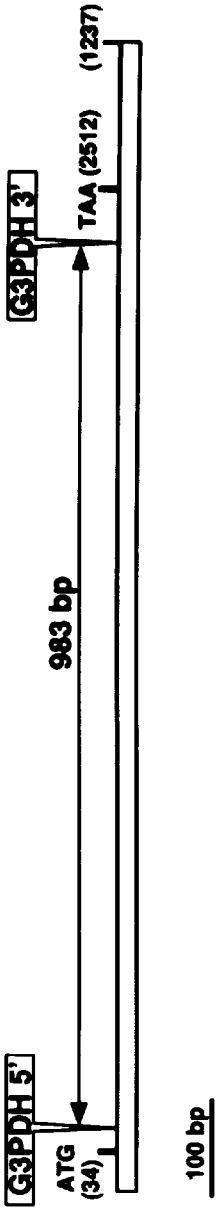
FIG. 2C is a cDNA map of glyceraldehyde 3-phosphate dehydrogenase.

Primers utilized in the initial or outside PCR amplification of PSA (PSA5' (SEQ ID No. 1) and PSA3' (SEQ ID No. 2)) were identical to those previously reported by Katz et al. (A. Lundwall and H. Lilja, Molecular cloning of the human prostate specific antigen cDNA, *FEBS Letters* 214:317–322 (1987)), that are located in exons 3 and 5 and span introns 3 and 4 (see FIGS. 2A–2C). Primers (PSAF1 (SEQ ID No. 3) and PSAR1 (SEQ ID No. 4)) for the nested inside PSA amplification were located 13 base pairs (bp) internal to PSA5' (SEQ ID No. 1) and 22 bp internal to PSA3' (SEQ ID No. 2) according to the published sequence of PSA. (A. Lundwall and H. Lilja, Molecular cloning of human prostate specific antigen cDNA. *FEBS Letters* 214:317–322 (1987).

by a serum PSA level greater than 20, a rising serum PSA level after hormonal treatment has been previously established, and a positive bone scan indicating metastasis. Women volunteers with no specific exclusion or inclusion criteria, and healthy male volunteers under the age of 40 were recruited from hospital employees.

RNA extraction

Blood (10 ml) was collected from prostate cancer patients and healthy volunteers in ethylene diaminetetraacetic acid (EDTA) tubes and immediately processed. Samples were centrifuged at 2000 rpm for 30 minutes, and the buffy coat cells were removed with a sterile transfer pipette. Total cellular RNA was isolated using TriZOL Reagent (Gibco/BRL). RNA was resuspended in RNAse-free (diethyl pyrocarbonate-treated) $H_2O$ and quantified by optical density at 260 nm. It should be understood that bone marrow samples may also be used in the process of the present invention.

Cell Culture

The human prostate cell line, LNCaP (ATCC CRL-1740) and human B-lymphocyte cell line ED1, were cultured in RPMI media containing 10% fetal bovine serum at 5% $CO_2$ and 37° C. Trypsin (0.5%) solution was used to disperse confluent LNCaP cultures for RNA isolation or subsequent passage.

cDNA First Strand Synthesis by Reverse Transcription

An aliquot containing 1.0 μg of total RNA was primed by random hexamers (2.5 μM) in the presence of RNAse inhibitor (1.0 U), 1 mM of each deoxynucleotide triphosphate, 2.5 U reverse transcriptase (Perkins Elmer), 1× PCR buffer II (Perkins Elmer), and 5.0 mM $MgCl_2$ in a final volume of 20 μl. The samples were incubated for 30 minutes at 42° C., followed by 5 minutes at 99° C. to heat inactivate the reverse transcriptase.

First Multiplex PCR Reaction

The first PCR reaction was done with one-half (10 μl) of the first strand cDNA product which was added to a master mix containing a final concentration of 1× PCR buffer II, 2 mM $MgCl_2$, 0.8 mM spermidine, 2.8% dimethyl sulfoxide (DMSO), 0.4 μM of each PSM primer (PSM5' (SEQ ID No. 5), and PSM3' (SEQ ID No. 6)), 0.3 μm of each PSA primer (PSA5' (SEQ ID No. 1) and PSA3' (SEQ ID No. 2), 0.3 μM of each G3PDH primer (G3PDH5 (SEQ ID No. 9) and G3PDH3' (SEQ ID No. 10), Clontech), in a total of 50 μl.

The total reaction mixture was then divided between two tubes (25 μl each), heated to 95° C. for 5 minutes after which 2.5 U of AmpliTaq polymerase (Perkin-Elmer) was added, and cycled at 94° C. (1 min.), 62° C. (1 min.), 72° C. (1 min.). One set of tubes was removed after 14 cycles for use as starting template for nested PCR, and the other set was amplified for a total of 35 cycles. Amplified products were visualized on a 2.0% agarose gel.

Second Multiplex PCR Reaction to Nest

The second multiplex reaction was done with 1.0 μl of amplified product from the initial PCR was removed from the tube amplified for 14 cycles and was added to a master mix containing a final concentration of 1× PCR buffer II, 2.0 mM $MgCl_2$, 0.2 mM dNTPs, 0.4 μM, 0.18 μM PSA inside primers (PSAF1 (SEQ ID No. 3) and PSAR1 (SEQ ID No. 4)), and 2.8% DMSO in a final volume of 50 μl. The tubes were heated to 95° C. for 5 minutes, 2.5 U of AmpliTaq polymerase was added, and amplified at 94° C. (1 min.), 62° C. (1 min), 72° C. (1 Min) for 33 cycles. Amplified products were visualized on a 2% agarose gel.

Southern Blot Hybridization Assay

Agarose gels were blotted to nylon membranes (Zetaprobe, Bio-Rad) by the Southern Blot procedure. (Sambrook et al, Molecular Cloning: A Laboratory Manual (1989), Cold Springs Harbor, N.Y.: Cold Springs Harbor Laboratory Press). After the filters were UV crosslinked, hybridizations were carried out using Rapid-hyp buffer (Amersham) using 30 pmol of $\tau$-$^{32}$P ATP labeled oligonucleotides (PSAF2 (SEQ ID No. 11), PSMAF2 (SEQ ID No: 12)) at 42° C. The filters were washed in 4×SSC, 0.1% SDS at 25° C. and exposed to Kodak XAR film.

PCR Fragment Cloning and Sequencing

PCR fragments were gel isolated, cloned into the pCRII vector (Invitrogen), and sequenced. Sequencing was performed on an ABI 373A automated DNA sequencer using the Taq dye deoxy cycle sequencing kit (ABI) as described by the manufacturer. DNA sequences obtained were analyzed, and sequence alignments were generated using Geneworks version 2.45 (Intelligenetics).

Results

Figure 3:
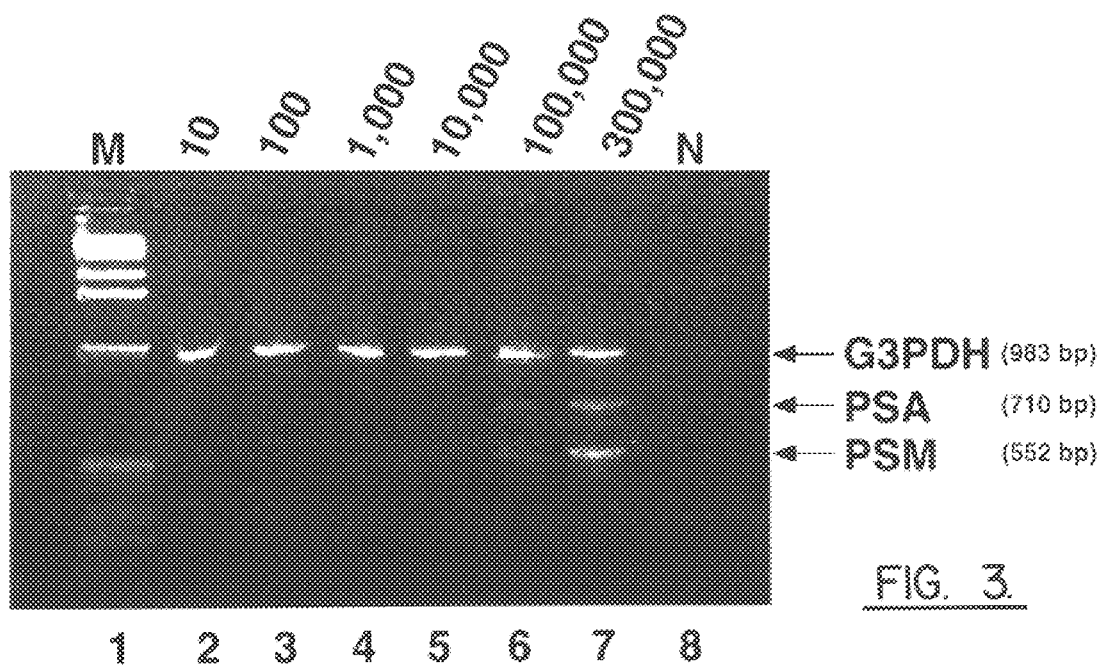
FIG. 3 illustrates the sensitivity of the multiplex RT-PCR assay as determined by diluted LNCaP cells. The human PSA and PSM-expressing cell line LNCaP was used as a positive control in the PCR reactions. Total RNA was extracted from serial diluted LNCaP cells in 10 million cultured B-lymphocytes that do not express PSA or PSM (data not shown). The RNA was then assayed by RT-PCR for the presence of prostate specific antigen (PSA) and prostate specific membrane antigen (PSM) using the 5' and 3' outside primers. Glyceraldehyde 3-phosphate dehydrogenase (G3PDH) was also amplified as an internal control. Amplified products were separated by 2% agarose gel electrophoresis and the results are shown. The number of diluted LNCaP cells appears above the gel, the sizes of the amplified products are indicated in parentheses, and the lane numbers appear below. N=no DNA negative control; M=molecular weight marker.
Figure 4:
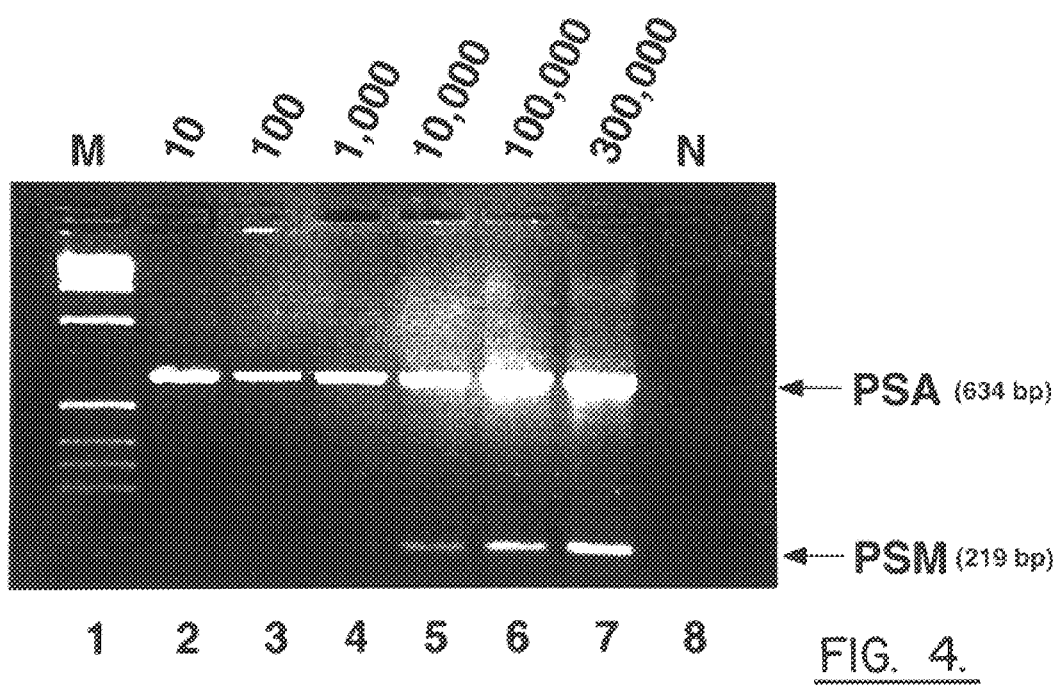
FIG. 4 shows the sensitivity of the nested multiplex PCR assay as determined by diluted LNCaP cells. 1.0 μl of amplified products (including the no DNA negative control) shown in FIG. 2 were used as templates for a second PCR amplification using F1 and R1 primers. The ethidium bromide stained 2- agarose gel is shown. The number of diluted LNCaP cells appears above the gel, the sizes of the amplified products are indicated in parentheses, and the lane numbers appear below. N=no DNA negative control; M=molecular weight marker.

Sensitivity of the Multiplex RT-PCR Assay As Determined by Diluted LNCaP Cells To determine the sensitivity of the multiplex RT-PCR assay, cells from the human PSA- and PSM-expressing prostate cell line, LNCaP, were serially diluted and added to 10 million cultured ED1 cells. ED1 cells are cultured B-lymphocytes that do not express either PSA or PSM (data not shown). Although it is likely that the amount of mRNA expression of cells cultured in vitro differ between laboratories and media conditions, all LNCaP cells used in this experiment were from the same cell passage. RNA was extracted from each LNCaP/ED1 mix and 1.0 μg was assayed by the multiplex PCR assay using random hexamers for the synthesis of the first cDNA strand, and the outside (5' and 3') primers for the subsequent PCR amplification. The amplified products were then resolved on a ethidium bromide stained 2% agarose gel which is shown in FIG. 3. The 983 bp amplified fragment of the positive PCR control, G3PDH, is visible in all lanes. PSA (710 bp) and PSM (552 bp) fragments are visible when the ratio of LNCaP cells to B-lymphocytes is at least 1:100 (lanes 6 and 7, FIG. 3).

Figure 5:
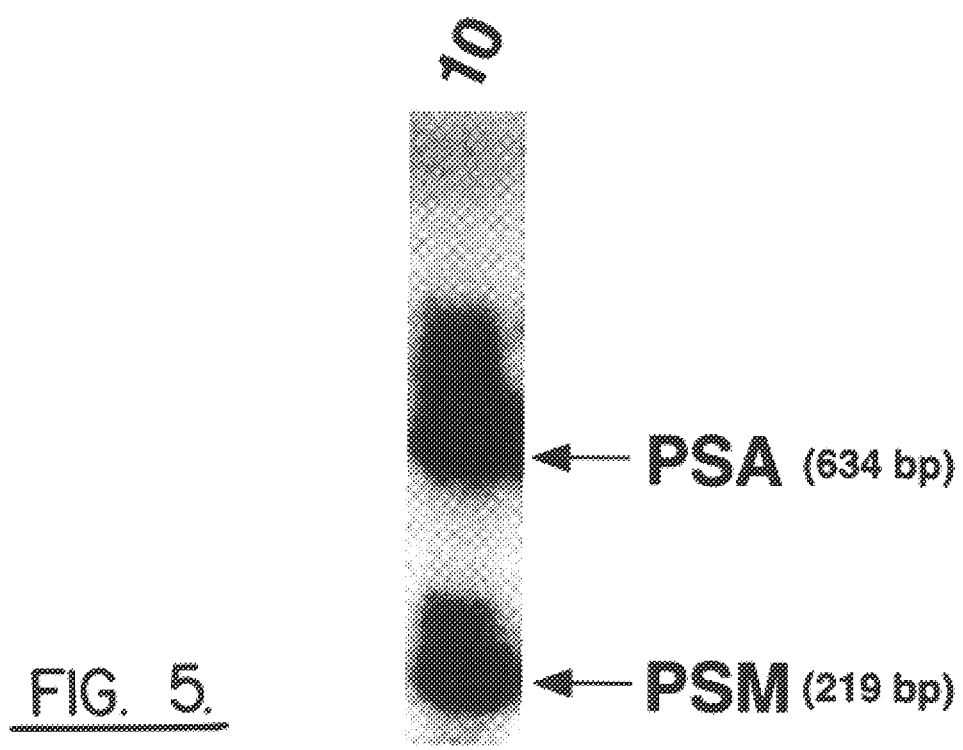
FIG. 5 illustrates PSM detected by Southern blot hybridization. Lane 1 from the gel shown in FIG. 3 was Southern blotted and hybridized with PSM (SEQ ID No. 12) and PSA (SEQ ID No. 11) specific probes. This indicates that one prostate cell from within one million B-lymphocytes can be amplified using the nested multiplex RT-PCR assay.

Nested multiplex PCR using the inside (F1 and R1) primers was then performed using 1.0 μl of amplified product from each outside reaction as the starting template. FIG. 3 shows the results of the nested multiplex assay. The appropriately sized fragment in the lane containing 10 LNCaP cells (lane 2) demonstrated that the multiplex PCR assay could easily detect 1 PSA-expressing cell from a background of 1 million cells. The appropriately sized PSM fragment was visible, albeit faint, in the lane containing 1000 LNCaP cells (lane 4) but not visible by ethidium bromide staining in the lane containing 10 LNCaP cells. The fragment was clearly detected, however, in lane 2 after Southern blot transfer and hybridization with an internal $^{32}$P end-labeled oligonucleotide probe, PSMF2, (SEQ ID No. 12) (FIG. 5, Table 1). This demonstrates that the nested PSM primers were also able to amplify a few as one LNCaP cell in a background of one million lymphocytes. Representative amplified fragments of PSA, PSM, and G3PDH were isolated from the gel and sequenced. The cDNA sequence of each amplified fragment aligned with the corresponding published cDNA sequence thus verifying the PCR products (data not shown).

Nested Multiplex RT-PCR of Prostate Cancer Patient and Control mRNA

Figure 6:
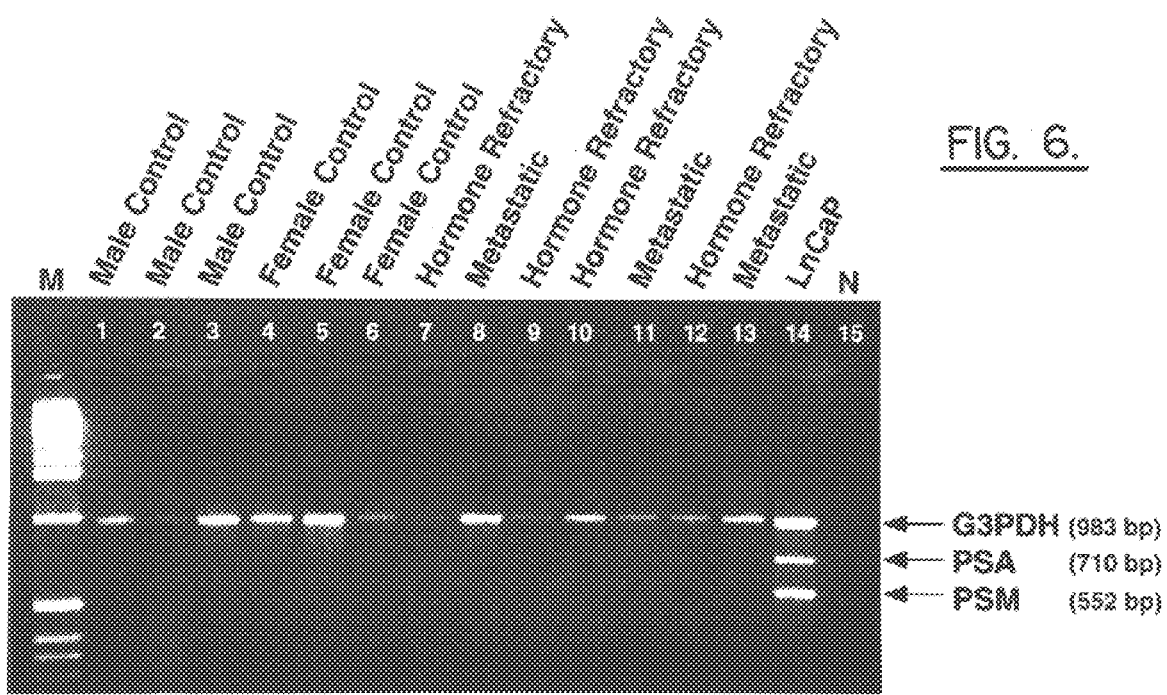
FIG. 6 shows a multiplex RT-PCR of prostate patient mRNA. Messenger RNA from prostate cancer patents and controls were assayed using the multiplex RT-PCR assay. Prostate samples were either from metastatic prostate patents or metastatic hormone-refractory patients. Control samples were provided by healthy volunteers. After amplification, the products were resolved on a 2% agarose gel. LNCaP RNA was used as a positive control for PSA and PSM. N=no DNA control; M=molecular weight marker.

Messenger RNA (mRNA) was isolated from blood samples collected from prostate cancer patients, healthy young male and female volunteers. Strict criteria for patient selection were used to insure the detection of circulating prostate cells and to help define the multiplex PCR assay conditions. The nested multiplex PCR assay used for the patient samples is summarized in FIG. 6. Briefly, 1.0 μg of total RNA was first synthesized into cDNA by reverse transcriptase in a 20 μl reaction volume. One-half of this RT reaction was placed into a tube containing 40 μl of a master mix that included all necessary PCR reagents. This master mix tube was then divided into two separate reactions, each containing 25 μl which were amplified for 35 and 14 cycles, respectively. Nested PCR was then performed using 1 μl of the 14 cycle amplified product as template, and all products from both initial and nested PCR were resolved on a 2% agarose gel.

Figure 7:
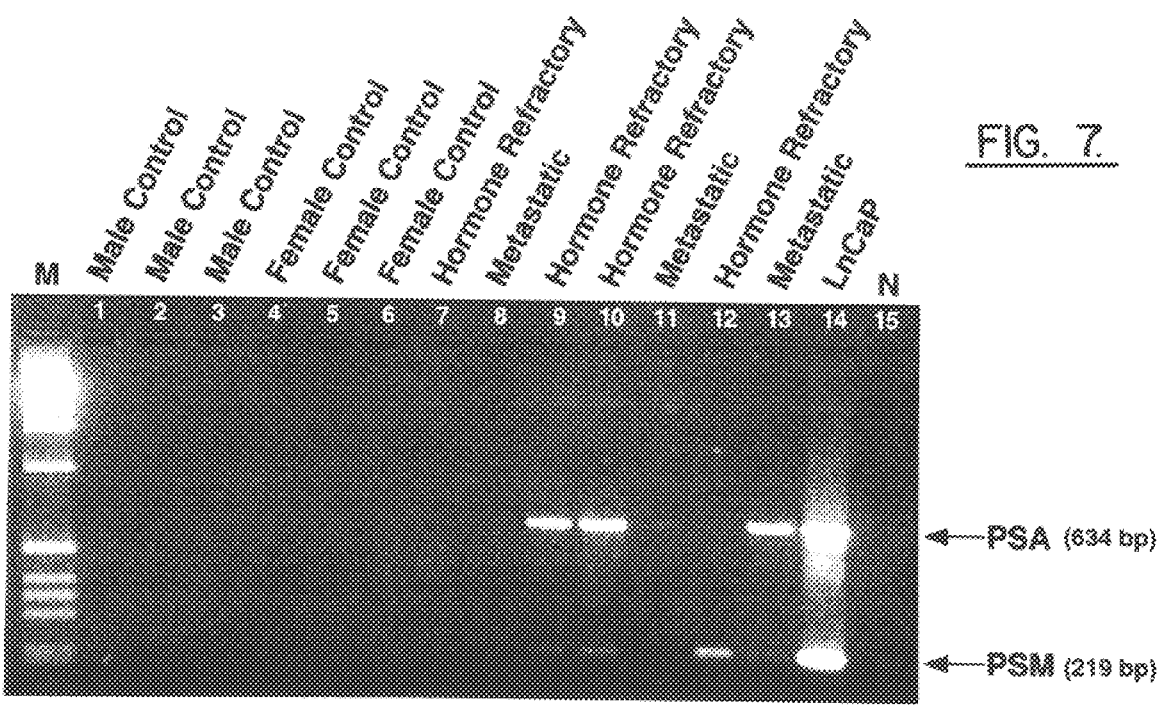
FIG. 7 is a representative Southern blot of nested multiplex PCR of prostate patient samples. 1.0 μl of each patient sample, including the no DNA control (N), was removed from the Multiplex RT-PCR tube after 14 cycles (see FIG. 1) and used as a template for a nested multiplex PCR reaction. Primers F1 and R1 were used in this nested PCR assay and the products were resolved on a 2% agarose gel. LNCaP cell RNA was used as a positive control for PSA and PSM. M=molecular weight marker.

The results after 35 cycles of the multiplex PCR assay utilizing the outside (5' and 3') primers on seven patient and six volunteer samples are shown in FIG. 7. Lanes 1–3 show the amplified fragments from the male controls, lanes 4–6 the amplified fragments from the female controls, and lanes 7–13 from the prostate cancer patients. 1.0 μg of RNA isolated from LNCaP cells was used as a positive control (lane 14) and 1 μl of water was used as a negative control. All lanes except the no template negative control were positive for G3PDH expression while PSA and PSM were amplified in the lane containing the LNCaP cells. This result indicates that no reaction failed due to unsuccessful PCR amplification. No PSA or PSM fragments were seen, however, in any patient lane after the initial amplification.

FIG. 7 shows the results of the nested multiplex PCR amplification from the seven prostate cancer patients and six volunteers. The lanes in FIG. 7 correspond to the same patient samples and lanes as in FIG. 6 after nested multiplex PCR amplification. Both PSA and PSM amplified fragments are clearly visible in two hormone-refractory patients (lanes 9 and 10), one metastatic patient (lane 13) and the LNCaP positive control (lane 14). PSA-expression alone was seen in one metastatic patient sample (lane 11), while in one metastatic hormone-refractory patient only PSM-expression was observed (lane 12). No amplified fragments were visible by ethidium bromide staining in any of the male or female control patients (lanes 1–6) or in two of the prostate cancer patients (hormone refractory lane 7, untreated metastatic lane 8). An additional 10 control samples (five male, five female) were also negative for PSA and PSM (data not shown). To verify that no amplified fragments were present that were undetectable by ethidium bromide staining alone, the gel in FIG. 7 was Southern blotted, and hybridized to radiolabeled oligonucleotide probes (PSAF2 (SEQ ID No: 11) and PSMF2 (SEQ ID No: 12)). None of the control samples were positive for either PSA or PSM expression by molecular hybridization (data not shown).

What is claimed is:

1. A method for detecting circulating prostate cells in a human, comprising:
   (a) obtaining a sample from a human;
   (b) isolating total cellular RNA;
   (c) synthesizing first strand CDNA;
   (d) performing a first multiplexing PCR step comprising adding a portion of said first strand EDNA product to a master mix containing prostate membrane antigen 5' and 3' outside primers and prostate specific antigen 5' and 3' outside primers, said prostate membrane antigen 5' outside primer having a sequence of SEQ ID NO. 5 and said prostate membrane antigen 3' outside primer having a sequence of SEQ ID NO. 6, adding polymerase to the mix, and amplifying;
   (e) performing a second multiplexing PCR step comprising adding a portion of the resulting mixture from step (d) to a second master mix containing prostate membrane antigen and prostate specific antigen 5' and 3' inside primers, adding polymerase to the mix and amplifying; and
   (f) determining the presence or absence of PCR product which corresponds to amplified prostate membrane antigen and prostate specific antigen cDNA fragment, and thereby the presence or absence of prostate cells in said sample.

2. The method according to claim 1 wherein said sample is a blood sample.

3. The method according to claim 1 wherein said sample is a bone marrow.

4. The method according to claim 1 wherein said method includes amplifying glyceraldehyde 3-phosphate dehydrogenase (G3PDH) cDNA as an internal PCR control.

5. The method according to claim 1 wherein said determining the presence or absence of PCR product is performed by subjecting said amplified portion to Southern hybridization with radio labeled probes for positive identification of amplified products.

6. The method according to claim 1 wherein said PSM 5' outside primer has a sequence of SEQ ID NO. 5, said PSM 3' outside primer has a sequence of SEQ ID NO. 6, and said PSA 5' outside primer has a sequence of SEQ ID NO. 1, and said PSA 3' outside primer has a sequence of SEQ ID NO. 2.

7. The method according to claim 1 wherein said PSM 5' inside primer has a sequence of SEQ ID NO. 7, and said PSM 3' inside primer has a sequence of SEQ ID NO. 8, and said PSA 5' inside primer has a sequence of SEQ ID NO. 3, said PSA 3' inside primer has a sequence of SEQ ID NO. 4.

8. A method for detecting circulating prostate cells in a human, comprising:
   (a) obtaining a sample from a human;
   (b) isolating total cellular RNA;
   (c) synthesizing first strand cDNA from said cellular RNA;
   (d) performing a first multiplexing PCR step in a reaction mixture which comprises a portion of said first strand cDNA, 3' and 5' prostate-specific membrane antigen outside primers, and 3' and 5' prostate-specific antigen outside primers, said 3' and 5' prostate-specific membrane antigen outside primers being specific to and hybridizable with, respectively, a first pair of sequences which are in opposing strands of the prostate-specific membrane antigen cDNA, said 3' and 5' prostate-specific antigen outside primers being specific to and hybridizable with, respectively, a second pair of sequences which are in opposing strands of the prostate-specific antigen CDNA, and at least one of two pairs of sequences being more than 400 base pairs apart along the opposing strands;
   (e) performing a second multiplexing PCR step in a second reaction mixture which comprises a portion of the resulting mixture in step (d), 3' and 5' prostate-specific membrane antigen inside primers, and 3' and 5' prostate-specific antigen inside primers, the size of the amplified prostate-specific membrane antigen cDNA fragment obtained by PCR using said 3' and 5' prostate-specific membrane antigen inside primers as primers and a prostate-specific membrane antigen cDNA as template differing by at least 90 base pairs from the size of the amplified prostate-specific antigen cDNA fragment obtained by PCR using said 3' and 5' prostate-specific antigen inside primers as primers and a prostate-specific antigen cDNA as template; and
   (f) detecting simultaneously in a single assay any amplified prostate membrane antigen cDNA and prostate specific antigen cDNA in the resulting mixture of step (e), and thereby identifying the presence or absence of prostate cells in said sample.

9. The method of claim 8, wherein said step of detecting simultaneously in a single assay any amplified prostate membrane antigen cDNA and prostate specific antigen cDNA comprises separating any said amplified prostate membrane antigen cDNA from any said prostate specific antigen cDNA PCR products by size difference in a gel and staining said gel.

10. The method of claim 9, wherein said gel is an agarose gel and said staining is ethidium bromide staining.

11. The method of claim 8, wherein said step of detecting simultaneously in a single assay any amplified prostate membrane antigen cDNA and prostate specific antigen cDNA comprises separating any said amplified prostate membrane antigen CDNA from any said prostate specific antigen cDNA by size difference in a gel and performing Southern hybridization.

12. A method for detecting circulating prostate cells in a human, comprising:
   (a) obtaining a sample from a human;
   (b) isolating total cellular RNA;
   (c) synthesizing first strand cDNA from said cellular RNA by reverse transcription;
   (d) performing a first multiplexing PCR step in a reaction mixture which comprises a portion of said first strand cDNA, and 6 primers having a sequence of SEQ ID NO. 1, 2, 5, 6, 9 and 10 respectively;
   (e) performing a second multiplexing PCR step in a second reaction mixture which comprises a portion of the resulting mixture in step (d), and 4 primers having a sequence of SEQ ID NO. 3, 4, 7 and 8 respectively, the number of nucleotides between SEQ ID NO. 3 and 4 in opposing strands of the prostate-specific membrane antigen cDNA, the number of nucleotides between SEQ ID NO. 7 AND 8 in opposing strands of the prostate-specific antigen cDNA, and the number of nucleotides between SEQ ID NO. 9 and 10 in opposing strands of the G3PDH cDNA being different from each other by at least 120 base pairs; and
   (f) detecting simultaneously in a single assay the presence of absence of amplified prostate membrane antigen cDNA, prostate specific antigen cDNA, and G3PDH cDNA fragment in the resulting mixture of step (e), and thereby identifying the presence or absence of prostate cells in said sample, comprising separating any said amplified cDNA from each other on a gel by size difference and performing Southern hybridization.

13. A diagnosis kit for detecting circulating prostate cells in a human, comprising a carrier being compartmentalized to receive in close confinement therein one or more container means, at least one container means containing primers having sequences of SEQ ID NO. 5, SEQ ID NO. 6, SEQ ID NO. 1, SEQ ID NO. 2, and at least another container means having primers having sequences of SEQ ID NO. 7, SEQ ID NO. 8, SEQ ID NO. 3, SEQ ID NO. 4.

* * * * *

UNITED STATES PATENT AND TRADEMARK OFFICE
CERTIFICATE OF CORRECTION

PATENT NO. : 5,858,673
DATED : January 12, 1999
INVENTOR(S) : Price et al.

It is certified that error appears in the above-identified patent and that said Letters Patent is hereby corrected as shown below:

Title page, Item [73], in the Assignee's name, before, "Charlotte, N.C." insert --d/b/a Carolinas Medical Center--.

In the References Cited, OTHER PUBLICATIONS, line 5, "337" should read --227--.

Column 13, line 6, "CDNA" should read --cDNA--; line 8, "EDNA" should read --cDNA--.

Column 14, line 3, "CDNA" should read --cDNA--; after "of" insert --the--.

Signed and Sealed this

First Day of June, 1999

Attest:

Q. TODD DICKINSON

*Attesting Officer*  *Acting Commissioner of Patents and Trademarks*